United States Patent [19]
Talma et al.

[11] Patent Number: 5,877,327
[45] Date of Patent: Mar. 2, 1999

[54] ANTI-FATIGUE COAGENTS FOR RUBBER VULCANIZATION

[75] Inventors: Auke Gerardus Talma, Bathmen; Rabindra Nath Datta, Deventer, both of Netherlands

[73] Assignee: Akzo Nobel N.V., Arnhem, Netherlands

[21] Appl. No.: 960,553

[22] Filed: Oct. 31, 1997

Related U.S. Application Data

[60] Continuation of Ser. No. 566,329, Dec. 1, 1995, abandoned, which is a division of Ser. No. 331,472, filed as PCT/EP93/01069, Apr. 28, 1993, Pat. No. 5,508,354.

[30] Foreign Application Priority Data

Apr. 29, 1992 [EP] European Pat. Off. .............. 92201187

[51] Int. Cl.$^6$ .................................................. C07D 207/00
[52] U.S. Cl. .......................................... 548/404; 548/531
[58] Field of Search ..................... 548/404, 531

[56] References Cited

U.S. PATENT DOCUMENTS

| | | | |
|---|---|---|---|
| 4,056,269 | 11/1977 | Pollitt et al. | 273/218 |
| 4,065,537 | 12/1977 | Miller et al. | 264/143 |
| 4,191,671 | 3/1980 | Kataoka et al. | 260/23.7 |
| 4,192,790 | 3/1980 | McKinstry et al. | 260/31.2 |
| 4,218,377 | 8/1980 | Stockinger et al. | 260/326.22 |
| 4,264,075 | 4/1981 | Miller et al. | 273/235 |

FOREIGN PATENT DOCUMENTS

| | | |
|---|---|---|
| 0 191 931 | 8/1986 | European Pat. Off. . |
| 0 390 012 | 10/1990 | European Pat. Off. . |
| 91/02048 | 2/1991 | WIPO . |

OTHER PUBLICATIONS

The Synthesis of Biscitraconimides and Polybiscitraconimides, Galanti, A. et al., *Journal of Polymer Science: Polymer Chemistry Edition*, vol. 19, 451–475 (1981).

The Synthesis of Bisitaconamic Acids and Isomeric Bisimide Monomers, *Journal of Polymer Science; Polymer Chemistry Edition*, vol. 20, 233–239, (1982).

*Derwent Abstract 95:8561*, Change in the structure and properties of vulcanizates based on natural rubber under prolonged vulcanization in the presence of vulcanizing systems containing sulfure and bismaleimides Chavchich, T.A. et al., *Kauchuk i Rezina*, vol. 4, pp. 20–23, 1998.

*Primary Examiner*—Bernard Lipman
*Attorney, Agent, or Firm*—Dilworth & Barrese

[57] ABSTRACT

Novel metal salts of (poly)citraconimide and (poly) itaconimide carboxylic acids, and a vulcanizable rubber composition comprising these novel metal salts and which, upon vulcanization, exhibits improved dynamic properties, are disclosed. Also disclosed are a sulfur-vulcanization process carried out in the presence of these metal salts and the product of said vulcanization process. The novel metal salts are represented by the formulas I and II:

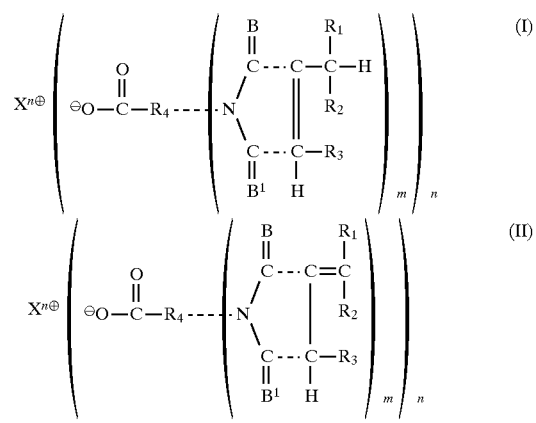

wherein $R_1$, $R_2$ and $R_3$ are independently selected from hydrogen, $C_1$–$C_{18}$ alkyl groups, $C_3$–$C_{18}$ cycloalkyl groups, $C_6$–$C_{18}$ aryl groups, $C_7$–$C_{30}$ aralkyl groups and $C_7$–$C_{30}$ alkaryl groups and $R_2$ and $R_3$ may combine to form a ring when $R_1$ is hydrogen; $R_4$ is selected from divalent, trivalent or tetravalent linear or branched radical chosen from a $C_1$–$C_{18}$ alkyl, $C_2$–$C_{18}$ alkenyl, $C_2$–$C_{18}$ alkynyl, $C_3$–$C_{18}$ cycloalkyl, $C_3$–$C_{18}$ polycycloalkyl, $C_6$–$C_{18}$ aryl, $C_6$–$C_{30}$ polyaryl, $C_7$–$C_{30}$ aralkyl, $C_7$–$C_{30}$ alkaryl, oligomers of one or more of these radicals, and which radicals may optionally contain one or more of oxygen, nitrogen, silicon, phosphorus, sulfur, sulphone, sulfoxy and boron; B and $B^1$ are independently selected from the following hetero atoms: oxygen and sulfur, X is a metal selected from Mg, Ti, Zn, Cd, Sr, Ba, Fe, V, Sn, Te, Mo, Mn, Pb and Al, m is an integer from 1–3 and n is an integer of from 2–4.

4 Claims, No Drawings

ANTI-FATIGUE COAGENTS FOR RUBBER VULCANIZATION

This is a continuation of application Ser. No. 08/566,329 filed on Dec. 1, 1995, now abandoned, which is a divisional application of U.S. application Ser. No. 08/331,472 filed Oct. 31, 1994, now U.S. Pat. No. 5,508,354, which is a 371 application of PCT/EP93/01069 filed Apr. 28, 1993.

This invention relates to novel metal salts of (poly) citraconimide and (poly)itaconimide carboxylic acids, and a vulcanizable rubber composition comprising these novel metal salts and which, upon vulcanization, exhibits improved dynamic properties. More particularly, the invention also relates to a sulfur-vulcanized rubber composition which is vulcanized in the presence of particular anti-fatigue coagents, as well as to a sulfur-vulcanization process carried out in the presence of said coagents and the use of these coagents In the sulfur-vulcanization of rubber.

In the tire and belt industries, among others, better mechanical and dynamic properties are being demanded. It has long been known that the physiomechanical and mechanical-dynamic properties of rubber can be improved by using a large amount of sulfur as a cross-linking agent. However, under service conditions or prolonged vulcanization, excess sulfur produces reversion which results in the shortening of crosslinks and a marked decrease in heat resistance and resistance to flex cracking, among other properties in the final product.

One of these problems, the resistance to flex cracking, also known as fatigue resistance, is solved by the addition of a coagent in accordance with the present invention.

In order to eliminate the foregoing disadvantage, It has been proposed to add saturated carboxylic acids and their metal salts to sulfur-vulcanization systems. One example of a publication relating to this subject is U.S. Pat. No. 4,191,671. In comparative Example 8 and Examples 11–23 improvements in fatigue resistance are shown which are said to result from the addition of stearic acid and salts of stearic acid with zinc, calcium, magnesium, aluminum, sodium and cobalt, to a sulfur-vulcanization system. This patent also mentions the addition of unsaturated carboxylic acid salts to a combination peroxide/sulfur vulcanization system in order to improve the abrasion resistance of the rubber.

European patent application 0 191 931 suggests that the use of a bis-maleimide compound in combination with a sulfonamide and a dithiophosphoric acid leads to further improvements in the mechanical and anti-reversion properties of sulfur-vulcanized rubbers. The patent specification claims that these rubbers exhibit improved resistance to reversion, resistance to heat ageing and resistance to flex cracking. However, this system is limited to vulcanization carried out in the presence of a sulfonamide accelerator in combination with a dithiophosphoric acid accelerator and is thus of limited utility in actual practice.

In the article, "Change in the Structure and Properties of Vulcanizates Based on Natural Rubber Under Prolonged Vulcanization in the Presence of Vulcanizing Systems Containing Sulfur and Bismaleimides," Chavchich, T. A., et al., *Kauchuk i Rezina*, vol. 4, pp. 20-3, 1981, there is disclosed that vulcanization of natural rubber tread stocks with sulfur in the presence of m-phenylenebis-maleimide at 143° C. over a 600-minute period gave vulcanizates with enhanced physical properties.

However, despite the fact that some of the above patents claim to reduce fatigue by addition of coagents, in actual practice, these systems fall short of the desired properties. For example, although stearic acid is widely used in the rubber industry, there remains a need for further improvements in the resistance to flex cracking for rubber articles which are subject to fatigue.

Accordingly, the present Invention provides novel compounds which, when employed in sulfur-vulcanization of rubber, lead to a significant, unexpected improvement in the fatigue properties of the vulcanized rubber composition. The novel compounds of the present invention are represented by the formulas I and II:

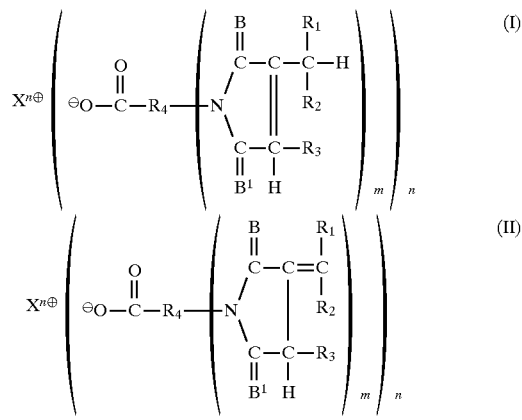

wherein $R_1$, $R_2$ and $R_3$ are independently selected from hydrogen, $C_1$–$C_{18}$ alkyl groups, $C_3$–$C_{18}$ cycloalkyl groups, $C_6$–$C_{18}$ aryl groups, $C_7$–$C_{30}$ aralkyl groups and $C_7$–$C_{30}$ alkaryl groups and $R_2$ and $R_3$ may combine to form a ring when $R_1$ is hydrogen; $R_4$ is selected from divalent, trivalent or tetravalent linear or branched radical chosen from a $C_1$–$C_{18}$ alkyl, $C_2$–$C_{18}$ alkenyl, $C_2$–$C_{18}$ alkynyl, $C_3$–$C_{18}$ cycloalkyl, $C_3$–$C_{18}$ polycycloalkyl, $C_6$–$C_{18}$ aryl, $C_6$–$C_{30}$ polyaryl, $C_7$–$C_{30}$ aralkyl, $C_7$–$C_{30}$ alkaryl, oligomers of one or more of these radicals, and which radicals may optionally contain one or more of oxygen, nitrogen, silicon, phosphorus, sulfur, sulphone, sulfoxy and boron; B and $B^1$ are independently selected from the following hetero atoms: oxygen and sulfur, X is a metal selected from Mg, Ti, Zn, Cd, Sr, Ba, Fe, V, Sn, Te, Mo, Mn, Pb and Al, m is an integer from 1–3 and n is an integer of from 2–4.

The present invention also encompasses sulfur-vulcanization processes carried out in the presence of at least one compound of the formulas I and 11, sulfur-vulcanized rubbers compositions made by such processes and the use of compounds of the formulas I and II as anti-fatigue coagents in the sulfur-vulcanization of rubbers.

The use of metal salts of, for example, methacrylic, maleic and betaphenyl acrylic acids in the vulcanization of rubber is known from European patent application 0 390 012. In this application, the zinc salts of methacrylic acid are preferred. Further, a combination sulfur/peroxide vulcanization system must be employed in order to achieve the object of this disclosure, namely products comprising both ionic and covalent crosslinks. This patent application does not mention the fatigue properties of the rubbers.

The use of zinc methacrylate and zinc salts of acrylic acid and cinnamic acid to reduce the Mooney viscosity in the compounded state of rubber compositions is also known from U.S. Pat. No. 4,192,790. These coagents are said to be useful in both sulfur and peroxide curing systems.

Further, it has been suggested to add a wide variety of metal salts of unsaturated carboxylic acids to elastomeric compositions used in the making of golf balls using a peroxide-based curing system. For example. U.S. Pat. Nos. 4,056,269; 4,065,537 and 4,264,075 suggest the use of salts of zinc. magnesium, calsium, lithium, sodium, potassium, cadmium, lead, barium, zirconium, berylium, copper, aluminum, tin, iron, antimony and bismuth with unsaturated carboxylic acids. Among the wide variety of unsaturated carboxylic acids mentioned are itaconic acid, maleic acid, substituted maleic acids, N-substituted maleamic acids, fumaric acid, crotonic acid and cinnamic acids. Also mentioned is the potential use of metal salts of maleimides and methylmaleimides. These compounds are said to improve several properties of the golf balls including durability, cannon life, sound and distance properties. However, few of these compounds are actually exemplified in these patents.

Finally, in non-prepublished International patent application publication number WO 92/07904, the use of biscitraconimides as anti-reversion coagents in the sulfur-vulcanization of rubber is disclosed. However, this application does not teach or suggest the use of metal salts of these materials and does not address the problem of resistance to flex cracking.

The present invention provides an excellent anti-fatigue effect without having a significant adverse effect on the remaining properties of the rubbers, when compared with similar sulfur-vulcanization systems using other coagents.

The present invention is applicable to all natural and synthetic rubbers. Examples of such rubbers include, but are not limited to, natural rubber, styrene-butadiene rubber, butadiene rubber, isoprene rubber, acrylonitrile-butadiene rubber, chloroprene rubber, isoprene-isobutylene rubber, brominated isoprene-isobutylene rubber, chlorinated isoprene-isobutylene rubber, ethylene-propylene-diene terpolymers, as well as combinations of two or more of these rubbers and combinations of one or more of these rubbers with other rubbers and/or thermoplastics.

Examples of sulfur which may be used in the present invention include various types of sulfur such as powdered sulfur, precipitated sulfur and insoluble sulfur. Also, sulfur donors may be used in place of, or in addition to sulfur in order to provide the required level of sulfur during the vulcanization process. Examples of such sulfur donors include, but are not limited to, tetramethylthiuram disulfide, tetraethylthiuram disulfide, tetrabutylthiuram disulfide, dipentamethylene thiuram hexasulfide, dipentamethylene thiuram tetrasulfide, dithiodimorpholine and mixtures thereof.

In this text, references to sulfur shall include sulfur donors and mixtures of sulfur and sulfur donors. Further, references to the quantity of sulfur employed in the vulcanization, when applied to sulfur donors, refer to a quantity of sulfur donor which is required to provide the equivalent amount of sulfur that is specified.

Anti-fatigue coagents of the present invention ore represented by the general formulas I & II. These coagents may be made by reacting a polycitraconic or polyitaconic imide acid with the oxide of the metal which is to be employed. In general, sufficient metal oxide is used to neutralize all of the polycitraconic or polyitaconic imide acid.

The imides of the present invention may be prepared by the methods disclosed in, "The synthesis of Biscitraconimides and Polybiscitraconimides," Galanti, A. V. and Scola, B. A., Journ. of Poly. Sci.: Polymer Chemistry Edition, Vol. 19, pp. 451–475, (1981); and "The Synthesis of Bisitaconamic Acids and Isomeric Bisimide Monomers," Galanti, A. V. et al., Journ. Poly. Sci.: Polymer Chemistry Edition, Vol. 20, pp. 233–239 (1982), by the use of (poly)amino carboxylic acids in place of the amine starting materials.

The resulting imido carboxylic acids are converted into the salts of the invention by addition of approximately equal equivalents of imido carboxylic acid and metal acetate to xylene and removal of acetic acid under reflux conditions using, for example, a Dean-Stark apparatus.

The preferred polycitraconic imide acid salts of the present invention represented by the formulas I and II include, the salts wherein $R_1=R_2=R_3=H$. In a more preferred embodiment, $B=B^1$-oxygen. In the most preferred embodiments, $R_4$ Is an alkyl, aryl or aralkyl group, m is 1, n is 2 and X is zinc or magnesium. The same preferences apply to the polyitaconic imide acid salts.

More specifically, the group $R_4$ mentioned in the formulas I and II is a divalent, trivalent or tetravalent linear or branched radical chosen from a $C_1-C_{18}$ alkyl, $C_2-C_{18}$ alkenyl, $C_2-C_{18}$ alkynyl, $C_3-C_{18}$ cycloalkyl. $C_3-C_{18}$ polycycloalkyl, $C_6-C_{18}$ aryl. $C_6-C_{30}$ polyaryl, $C_7-C_{30}$ aralkyl, $C_7-C_{30}$ alkaryl, oligomers of one or more of these radicals, and which radicals may optionally contain one or more of oxygen, nitrogen, silicon, phosphorus, sulfur, sulphone, sulfoxy and boron.

More specific examples of some of the imide compounds useful in the present invention include, but are not limited to, the following:

Zinc Bis-(N-carboxymethyl-citraconimide)

Zinc Bis-(N-2-carboxyethyl-citraconimide)

Zinc Bis-(N-3-carboxypropyl-citraconimide)

Zinc Bis-(N-4-carboxybutyl-citraconimide)

Zinc Bis-(N-5-carboxypentyl-citraconimide)

Zinc Bis-(N-6-carboxyhexyl-citraconimide)

Zinc Bis-(N-7-carboxyheptyl-citraconimide)

Zinc Bis-(N-8-carboxyoctyl-citraconimide)

Zinc Bis-(N-9-carboxynonyl-citraconimide)

Zinc Bis-(N-10-carboxydecyl-citraconimide)

Zinc Bis-(N-11carboxyundecyl-citraconimide)

Zinc Bis-(N-12-carboxydodecyl-citraconimide)

Zinc Bis-(N-4-carboxyphenyl-citraconimide)

Zinc Bis-(N-3-carboxyphenyl-citraconimide)

Zinc Bis-(N-2-carboxyphenyl-citraconimide)

Zinc Bis-(N-(1-carboxy-2-methyl)propyl-citraconimide)

Zinc sis-(N-(4-carboxyphenyl)methyl-citraconimide)

Zinc Bis-(N-α-acetoxyphenyl-citraconimide)

Zinc Bis-(N-(4-glyoxy-2-thiazolyl)-citraconimide)

Zinc Bis-(N-(4-carboxy-3-pyrazoyl)-citraconimide)

Zinc Bis-(N-(3-carboxy-4-nitro)phenyl-citraconimide)

Zinc Bis-(N-(1-carboxy-3-hydroxy)phenyl-citraconimide)

Zinc Bis-(N-(3-carboxy-2-pyridinyl)-citraconimide)

Zinc Bis-(N-(1-carboxy-1-tertiary-butyl)methyl-citraconimide)

Zinc Bis-(N-(1-carboxy-2,2-dimethyl)propyl-citraconimide)

Zinc Bis-(N-tertiary-leucinyl-citraconimide)

Zinc Bis-(N-(2-carboxy-4-hydroxy)phenyl-citraconimide)

Zinc Bis-(N-(2-carboxy-2-propenyl)-citraconimide)

Zinc Bis-(N-(1-carboxy-4-hydroxy)phenyl-citraconimide)

Zinc Bis-(N-1-carboxypropyl-citraconimide)

Zinc Bis-(N-1-carboxybutyl-citraconimide)

Zinc Bis-(N-1-carboxypentyl-citraconimide)

Zinc Bis-(N-1-carboxyethyl-citraconimide)

Zinc Bis-(N-(2-carboxy-4-chloro)phenyl-citraconimide)

Zinc Bis-(N-(2-carboxy-4-bromo)phenyl-citraconimide) .

Zinc Bis-(N-(2-carboxy-fluoro)phenyl-citraconimide)

Zinc Bis-(N-(2-carboxy-4,6-dichloro)phenyl-citraconimide)

Zinc Bis-(N-(3-carboxy-phenyl-1,5-diyl)-biscitraconimide)

Zinc Bis-(N-(2-carboxy-1-(4-hydroxyphenyl)propyl)-citraconimide)

Zinc Bis-(N-(2-carboxy-2-propyl)-citraconimide)

Zinc Bis-(N-oxamoyl-citraconimide)

Zinc Bis-(N-(1-carboxy-4-naphthyl)-citraconimide)

Zinc Bis-(N-(1-carboxy-2-methyl)butyl-citraconimide)

Zinc Bis-(N-(1-carboxy-3-methyl)butyl-citraconimide)

Zinc Bis-(N-(1-carboxy-4-thia)pentyl-citraconimide)

Zinc Bis-(N-(1-carboxypentyl-1,5-diyl)biscitraconimide)

Zinc Bis-(N-1-carboxy-2-methyl)propyl-citraconimide)

Zinc Bis-(N-(4-acetoxy-2-thiazolyl)-citraconimide)

Zinc Bis-(N-1-carboxyheptyl-citraconimide)

Zinc Bis-(N-1-carboxyhexyl-citraconimide)

Zinc Bis-(N-(1-carboxy-1,4-butyl)-biscitraconimide)

In the foregoing list of examples, zinc can of course be substituted by any other metal selected from Mg, Ti, Zn, Cd, Sr, Ba, Fe, V, Sn, Te, Mo, Mn, Pb and Al, and the valence of the metal will determine if the salt is a bis., tris- or tetra-salt. Further, in all cases, the citraconimide can also be replaced by an itaconimide to obtain the itaconimide salts of the present invention.

The amount of sulfur to be compounded with the rubber is, based on 100 parts of rubber, usually 0.1 to 25 parts by weight, and more preferably 0.2 to 8 parts by weight. The amount of sulfur donor to be compounded with the rubber is an amount sufficient to provide an equivalent amount of sulfur which is the same as if sulfur itself were used.

The amount of anti-fatigue coagent to be compounded with the rubber is, based on 100 parts of rubber, 0.1 to 5 parts by weight, and more preferably 0.2 to 3.0 parts by weight. These ingredients may be employed as a pre-mix, or added simultaneously or separately, and they may be added together with other rubber compounding Ingredients as well.

In most circumstances it is also desirable to have a vulcanization accelerator in the rubber compound. Conventional, known vulcanization accelerators may be employed. The preferred vulcanization accelerators include mercaptobenzothiazole, 2,2'-mercaptobenzothiazole disulfide, sulfonamide accelerators including N-cyclohexyl-2-benzothiazole sulfonamide, N-tertiary-butyl-2-benzothiazole sulfonamide, N,N'-dicyclohexyl-2-benzothiazole sulfonamide, and 2-(morpholinothio)benzothiazole; thiophosphoric acid derivative accelerators, thiurams, dithiocarbamates, diphenyl guanidine, diorthotolyl guanidine, dithiocarbamylsulfonamides, xanthates, triazine accelerators and mixtures thereof.

When the vulcanization accelerator is employed, quantities of from 0.1 to 8 parts by weight, based on 100 parts by weight of rubber composition, are used. More preferably, the vulcanization accelerator comprises 0.3 to 4.0 parts by weight, based on 100 parts by weight of rubber.

Other conventional rubber additives may also be employed in their usual amounts. For example, reinforcing agents such as carbon black, silica, clay, whiting and other mineral fillers, as well as mixtures of fillers, may be Included in the rubber composition, Other additives such as process oils, tackifiers, waxes, antioxidants, antiozonants, pigments, resins, plasticizers, process aids, factice, compounding agents and activators such as stearic acid and zinc oxide may be included in conventional, known amounts. For a more complete listing of rubber additives which may be used in combination with the present invention see, W. Hofmann, "Rubber Technology Handbook," Chapter 4, Rubber Chemicals and Additives, pp. 217–353, Hanser Publishers, Munich 1989.

Further, scorch retarders such as phthalic Anhydride, pyromellitic anhydride, benzene hexacarboxylic trianhydride, 4-methylphthalic anhydride, trimellitic anhydride, 4-chlorophthalic anhydride, N-cyclohexyl-thiophthalimide, salicylic acid, benzoic acid, maleic anhydride and N-nitrosodiphenylamine may also be included in the rubber composition in conventional, known amounts. Finally, in specific applications it may also be desirable to include steel-cord adhesion promoters such as cobalt salts and dithiosulfates in conventional, known quantities.

The present Invention also relates to a vulcanization process which comprises the step of vulcanizing at least one natural or synthetic rubber in the presence of 0.1 to 25 parts by weight of sulfur or a sulfur donor per 100 parts by weight of rubber, characterized in that said process is carried out In the presence of an effective amount of an anti-fatigue coagent represented by the formulas I and II.

The process is carried out at a temperature of 110°–220° C. over a period of up to 24 hours. More preferably, the process is carried out at a temperature of 120°–190° C. over a period of up to 8 hours in the presence of 0.1 to 5.0 parts by weight of anti-fatigue coagent. Even more preferable is the use of 0.2–3.0 parts by weight of anti-fatigue coagent. All of the additives mentioned above with respect to the rubber composition may also be present during the vulcanization process of the invention.

In a more preferred embodiment of the vulcanization process, the vulcanization is carried out at a temperature of 120°–190° C. over a period of up to 8 hours and in the presence of 0.1 to 8.0 parts by weight, based on 100 parts by weight of rubber, of at least one vulcanization accelerator.

The present invention also comprises the use of a compound of the formulas I and II as an anti-fatigue coagent in the sulfur-vulcanization of rubber. Finally, the present invention also includes articles of manufacture, such as tires, which comprise sulfur-vulcanized rubber which is vulcanized in the presence of the anti-fatigue coagents of the present invention.

The invention is further illustrated by the following examples which are not to be construed as limiting the invention in any way. The scope of the invention is to be determined from the claims appended hereto.

EXPERIMENTAL METHODS USED IN THE EXAMPLES

Compounding, Vulcanization and Characterization of Compounds

In the following examples, rubber compounding, vulcanization and testing was carried out according to standard methods except as otherwise stated:

Base compounds were mixed in a Farrel Bridge BR 1.6 liter Banbury type internal mixer (preheating at 50° C., rotor speed 77 rpm, mixing time 6 min with full cooling).

Vulcanization ingredients and coagents were added to the compounds on a Schwabenthan Polymix 150 L two-roll mill (friction 1:1.22, temperature 70° C., 3 min).

Cure characteristics were determined using a Goettfert elastograph or Monsanto rheometer ODR (arc 1) or MDR 2000E (arc 0.51): delta torque or extent of crosslinking (em) is the maximum torque (MH, also denoted as initial torque maximum, $T_1$) minus the minimum torque (ML). Scorch safety ($t_s2$) is the time to 2% of delta torque above minimum torque (ML), optimum cure time ($t_{90}$) is the time to 90% of delta torque above minimum, reversion time ($t_r2$) is the time to 2% of delta torque below maximum torque. Final torque ($T_f$) is the torque measured after the overcure time.

Sheets and test specimens were vulcanized by compression molding in a Fontyne TP-400 press.

Fatigue to failure was determined using a Monsanto FTFT tester (cam 14; ASTM D 4482).

EXAMPLES 1–2 AND COMPARATIVE EXAMPLES A–D

Two different anti-fatigue agents in accordance with the present invention were prepared and tested in the sulfur vulcanization process according to the present invention. The citraconic acid salts employed are listed in Table 1. These coagents were compared with a system with no coagent (control), the zinc salt of a monocitraconimide (MCI-CPHZ), Duralink® HTS and a meta-xylylene biscitraconimide coagent (BCI-MX).

The formulations were cured at 150° C. or 170° C. until $t_{90}$ was reached.

The accelerator employed was n-cyclohexyl-2-benzothiazole sulfonamide (CBS). Comparative example B was a control example with no anti-fatigue additive. Natural rubber was vulcanized in the presence of the foregoing compounds using the formulations listed in Table 1.

The results of fatigue to failure data are given in Tables 2 and 3. Details on other physical properties art given in Table 4.

TABLE 1

| Recipes | Compound Composition | | | | |
|---|---|---|---|---|---|
| | A | B | C | 1 | 2 |
| Ingredients | | | | | |
| NR SMR CV | 100 | 100 | 100 | 100 | 100 |
| Carbon black N-330 | 50 | 50 | 50 | 50 | 50 |
| Stearic Acid | 2 | 2 | 2 | 2 | 2 |
| Zinc Oxide | 5 | 5 | 5 | 5 | 5 |
| Aromatic Oil (Ingralen ® 150) | 3 | 3 | 3 | 3 | 3 |
| Perkacit ® CBS | 0.6 | 0.6 | 0.6 | 0.6 | 0.6 |
| Sulfur | 2.3 | 2.3 | 2.3 | 2.3 | 2.3 |
| Duralink ® HTS | — | 1.0 | — | — | — |
| BCI-MX | — | — | 1.0 | — | — |
| BCI-CMZ | — | — | — | 1.0 | — |
| BCI-CPhz | — | — | — | — | 1.0 |

Structures of the BCI—Zn salts

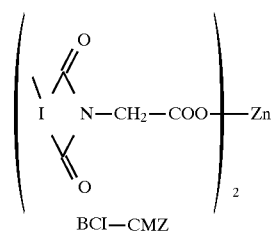

BCI—CMZ

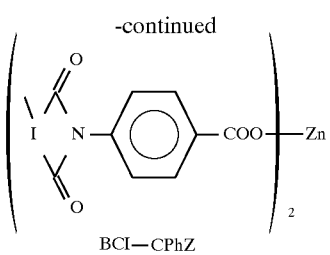

BCI—CPhZ

TABLE 2

Failure Properties of The Vulcanizates cured at 150° C. for t90 Monsanto Fatigue to Failure Data

| Recipes | No of Kilocycles to failure |
|---|---|
| A (CONTROL) | 25.8 |
| B (HTS) | 27.6 |
| C (BCI-MX) | 23.6 |
| 1 (BCI-CMZ) | 48.8 |
| 2 (BCI-CPhZ) | 53.9 |

TABLE 3

Failure Properties of The Vulcanizates cured at 170° C. for t90 Monsanto Fatigue to Failure Data

| Recipes | No of Kilocycles to failure |
|---|---|
| A (CONTROL) | 24.6 |
| B (HTS) | 27.2 |
| C (BCI-MX) | 25.2 |
| 1 (BCI-CMZ) | 42.6 |
| 2 (BCI-CPhZ) | 44.2 |

TABLE 4

| | Modulus: (MPa) | | | Tensile | |
|---|---|---|---|---|---|
| | 50% | 100% | 300% | Strength (MPa) | Elongation (%) |
| A (Control) | 1.74 | 3.74 | 17.92 | 24.40 | 406 |
| B (HTS) | 1.69 | 3.39 | 16.94 | 25.21 | 428 |
| C (BCI-MX) | 1.64 | 3.34 | 16.50 | 24.91 | 433 |
| 1 (BCI-CMZ) | 1.74 | 3.60 | 17.09 | 25.32 | 480 |
| 2 (BCI-CPhZ) | 1.78 | 3.51 | 16.68 | 25.10 | 465 |

EXAMPLES 3–4

The procedure of Examples 1–2 was repeated using the formulations given in Table 5, The properties of the cured rubber were measured and can be found in Table 6.

TABLE 5

| Ingredients | Control | 3 | 4 |
|---|---|---|---|
| NR SMR CV | 100 | 100 | 100 |
| Carbon Black N-330 | 50 | 50 | 50 |
| Stearic Acid | 3 | 3 | 3 |
| Zinc Oxide | 5 | 5 | 5 |
| Aromatic Oil | | | |

TABLE 5-continued

| Ingredients | Control | 3 | 4 |
| --- | --- | --- | --- |
| (Ingrelen 150) | 3 | 3 | 3 |
| Perkacit ® CBS | 0.6 | 0.6 | 0.6 |
| Sulfur | 2.3 | 2.3 | 2.3 |
| BCI-CMZ | — | 2.0 | — |
| BCI-CMMg | — | — | 2.0 |

BCI-CMMg is the same as BCI-CMZ except that the zinc ion is replaced by a magnesium ion.

TABLE 6

| Example | Extent of Cosslinking (Nm) | ts2 (min) | t90 (min) | Kilocycles to failure cured at 150° | cured at 170° C. |
| --- | --- | --- | --- | --- | --- |
| Control | 1.59 (1.42) | 4.79 (1.11) | 13.6 (3.1) | 24.9 | 22.9 |
| 3 | 1.68 (1.47) | 5.58 (1.21) | 18.3 (4.3) | 46.8 | 43.0 |
| 4 | 1.70 (1.40) | 5.55 (1.23) | 16.7 (4.3) | 32.7 | 30.7 |

Values in parenthesis are for curing at 170° C. Other values are for curing at 150° C.

These examples demonstrate the anti-fatigue properties of the zinc and magnesium salts of the invention.

The foregoing examples were presented for the purpose of illustration and description only and are not to be construed as limiting the scope of the invention in any way. The scope of the invention is to be determined from the claims appended hereto.

What is claimed is:

1. A compound represented by the following formula:

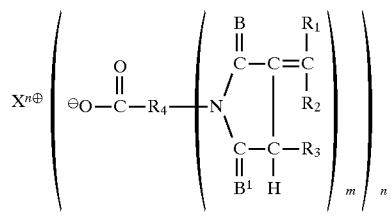

wherein $R_1$ and $R_2$ are independently selected from hydrogen, $C_1$–$C_{18}$ alkyl groups, $C_3$–$C_{18}$ cycloalkyl groups, $C_6$–$C_{18}$ aryl groups, $C_7$–$C_{30}$ aralkyl groups and $C_7$–$C_{30}$ alkaryl groups, $R_3$ is hydrogen or $R_2$ and $R_3$ may combine to form a ring when $R_1$ is hydrogen; $R_4$ is selected from divalent, trivalent or tetravalent linear or branched radical chosen from a $C_1$–$C_{18}$ alkyl, $C_2$–$C_{18}$ alkenyl, $C_2$–$C_{18}$ alkynyl, $C_3$–$C_{18}$ cycloalkyl, $C_3$–$C_{18}$ polycycloalkyl, $C_6$–$C_{18}$ aryl, $C_6$–$C_{30}$ polyaryl, $C_7$–$C_{30}$ aralkyl, $C_7$–$C_{30}$ alkaryl, oligomers of one or more of these radicals, and which radicals may optionally contain one or more of oxygen, nitrogen, silicon, phosphorous, sulfur, sulphone, sulfoxy and boron; B and $B^1$ are independently selected from the following heteroatoms: oxygen and sulfur, X is a metal selected from Mg, Ti, Zn, Cd, Sr, Ba, Fe, V, Sn, Te, Mo, Mn, Pb and Al, m is an integer from 1–3 and n is an integer of from 2–4.

2. A compound as claimed in claim 1 wherein $R_1$, $R_2$ and $R_3$ are hydrogen, and B and $B^1$ are oxygen.

3. A compound as claimed in claim 1 wherein $R_4$ is selected from methylene, ethylene, pentamethylene, isopropylmethylene and phenylene.

4. A compound as claimed in claim 1 wherein n is 2 and X is selected from Zn and Mg.

* * * * *